United States Patent
Dambal et al.

(10) Patent No.: US 6,757,977 B2
(45) Date of Patent: Jul. 6, 2004

(54) DISPOSABLE SURGICAL SAFETY SCALPEL

(75) Inventors: Siddappa Hanamantappa Dambal, New Delhi (IN); Lutfur Rehman, New Delhi (IN); Krishna Deo Kehr, New Delhi (IN)

(73) Assignee: Jai Surgicals Limited (IN)

( * ) Notice: Subject to any disclaimer, the term of this patent is extended or adjusted under 35 U.S.C. 154(b) by 0 days.

(21) Appl. No.: 10/055,627

(22) Filed: Jan. 25, 2002

(65) Prior Publication Data

US 2003/0093905 A1 May 22, 2003

(30) Foreign Application Priority Data

Nov. 20, 2001 (IN) .................................. 1163/DEL/2001

(51) Int. Cl.⁷ ............................................. A61B 17/32
(52) U.S. Cl. ............................ 30/162; 30/335; 606/167
(58) Field of Search .................. 30/162, 335; 606/166, 606/167, 170

(56) References Cited

U.S. PATENT DOCUMENTS

| | | | |
|---|---|---|---|
| 2,735,176 A | | 2/1956 | Costin |
| 3,905,101 A | * | 9/1975 | Shepherd ..................... 30/162 |
| 3,906,626 A | | 9/1975 | Riuli |
| 5,342,379 A | * | 8/1994 | Volinsky ..................... 606/167 |
| 5,344,424 A | * | 9/1994 | Roberts et al. ............. 606/167 |
| 5,431,672 A | * | 7/1995 | Cote et al. .................. 606/167 |
| 5,531,754 A | | 7/1996 | Shackelford, Sr. |
| 5,599,351 A | * | 2/1997 | Haber et al. ................ 606/167 |

* cited by examiner

Primary Examiner—Hwei-Siu Payer
(74) Attorney, Agent, or Firm—Nixon & Vanderhye PC

(57) ABSTRACT

The present invention relates to a disposable surgical safety scalpel with a retractable blade inside a hollow handle with a novel locking and unlocking arrangement that enables easy use and ensures safety in pre-use, use, and post-use conditions.

18 Claims, 3 Drawing Sheets

DISPOSABLE SURGICAL SAFETY SCALPEL

FIELD OF THE INVENTION

The present invention relates to a disposable surgical safety scalpel. More particularly, the present invention relates to a disposable surgical safety scalpel with a retractable blade inside a hollow handle with a novel locking and unlocking arrangement that enables easy use and ensures safety in pre-use, use, and post-use conditions.

BACKGROUND OF THE INVENTION

Scalpels are widely used in surgery the world over. Surgical scalpels have sharp cutting edges on the blades, which makes them dangerous to use for the surgical team. The potential for accidents when for example the scalpel is being passed back and forth during an operation, is very high. Similarly during post-use, the disposal of the scalpel also poses a problem, in that the slightest negligence during handling in the postoperative time frame can also result in accidents unless extreme care is exercised.

In recent years, the spread of communicable diseases such as Hepatitis, AIDS and such other diseases makes it important to ensure that safety features are built into the surgical scalpel such that the potential for accidental harm be falling the handler or any person in the vicinity, inadvertently is minimized. A study by Dr. Jannie Jagger in April 1995 on the "Advances in exposure prevention" published by International Health Care Workers and Safety, Research and Resource Center, shows that 34% of scalpel wounds occur during the use of the scalpel in an operative procedure, while 39% occurs when the scalpel is passed from hand to hand during an operation, and the balance 27% when disposal of the scalpel is being effected.

Hepatitis—B, AIDS and other blood carried diseases all can be communicated during the operative stage. Since detection and treatment of the above diseases is not possible at the time that a scalpel used accidentally cuts or nicks a person, the normal presumption is that all the persons who are involved in an operative procedure are exposed to risk of infection. Additionally, to ensure that injury is not caused during the disposal stage of the scalpel, it must be ensured that the blade is suitably inaccessible and protected such that the disposal of the scalpel is made free of the potential for injury.

Several methods are provided in the art to ensure that the scalpel during all of pre-use, use and post-use conditions is safe and does not cause accidental harm to the handler.

In the art, surgical scalpels have been provided with a blade shield or guard in order to ensure that the safe packaging of the product and thus its sterility is maintained. But the solution does not take care of the problem in the use and post operative stage.

U.S. Pat. No. 2,735,176 discloses a surgical knife that is provided with a hollow handle which functions as a sheath for the blade that is extendable slidingly and retractable between a first cutting position and a second shielded position. Movement of the blade requires the surgeon to positively act to at least rearrange the handle in his/her hand. In some embodiments, it requires a two-handed actuation of the shield to ensure that the blade is properly sheathed before transfer to another person. Another disadvantage of the sheath system for surgical knives is that they require complex locking and retraction mechanisms. Such mechanisms often prove to be extremely fragile and expensive to incorporate resulting in an increase in cost of manufacture. The increased cost of manufacture of such scalpels renders the disposal factor not very attractive for the user. Similar to the scalpel disclosed in the above patent, U.S. Pat. Nos. 3,905, 101 and 3,906,626 disclose sheaths wherein the handle carrying the blade is slideble from a first protective position to a second cutting position and vice versa. However, to initiate the sliding action, two-handed actuation is required rendering the instrument user unfriendly.

OBJECTS OF THE INVENTION

The main object of the present invention is to provide a disposable safety scalpel wherein the blade is protected from exposure during pre- and post-use conditions.

It is another object of the present invention to provide a disposable safety scalpel where bringing the cutting edge of the blade into the operational mode requires a specific actuation by the user.

It is another object of the present invention to provide a disposable safety scalpel with a retractable blade that is user friendly and with a firm locking arrangement to ensure safety in handling during operative stage.

It is another object of the present invention to provide a disposable safety scalpel where the potential for pre- and post-operative accidental injury to the user or to other persons in the vicinity are completely eliminated or substantially minimized.

It is a further object of the invention to provide a disposable safety scalpel with a permanent locking mechanism in the post use stage to ensure total or at least substantial safety in disposal of the scalpel post—use.

SUMMARY OF THE INVENTION

Accordingly, the present invention provides a disposable safety scalpel comprising a housing with a proximal open end to enable sliding in and out of the blade carrier to expose the cutting edge of the scalpel blade and a distal closed end, a blade carrier slideably provided in such housing, said blade carrier being provided with a scalpel blade fixedly located on one end thereof, the other end of the blade carrier being provided with a plurality of locking means to enable locking of the blade in three positions of pre-use, actual use and post use disposal stage, said blade carrier also being provided with a sliding means to enable movement of the blade carrier within the housing, the housing being provided with lock cooperating mechanisms at three positions thereon corresponding to pre-use, use and post-use disposal stages, said lock cooperating mechanisms cooperating with the respective locking means provided on said blade carrier during use.

In one embodiment of the invention, the blade carrier is provided with actuating means to enable positive movement of the blade carrier from a first pre-use stage to an actual use stage and finally to a post-use disposal stage.

In another embodiment of the invention, the first locking mechanism for the pre-use stage comprises of at least one lug provided on the blade carrier and cooperating with a depression provided on said housing to ensure pass locking.

In another embodiment of the invention, the second in-use locking mechanism comprises of at least a pair of matched arms extending in the longitudinal direction from the end of the blade carrier opposite the blade end and provided with lugs cooperating with a corresponding second pair of slots provided in the flange on said housing, said pair of slots being adapted to receive the lugs on said arms and retain them therein permanently till actual release by the user.

In a further embodiment of the invention, the second in-use locking mechanism is provided with an actuating means to enable release of the blade carrier from the use position to the pass position by natural action of retraction.

In a further embodiment of the invention, the third arm provided on the said blade carrier to ensure permanent locking of the blade by wedge locking it to the end piece in the post use disposal stage.

In another embodiment of the invention, the housing is provided with a groove running on one side thereon to enable sliding movement of the blade carrier thereon from a pass position to a in use position as required during operation, and to a third permanent locking position for the post-use disposal stage.

In another embodiment of the invention, the blade carrier is provided with a actuating means to enable movement of the blade carrier from the pass to in use stage and finally to a post-use disposal stage.

In a further embodiment of the invention, the actuating means provided on said blade carrier comprises a knob.

In another embodiment of the invention, the slots on the housing are adapted to receive the said second locking mechanism and the third locking mechanism are provided respectively on opposite sides of the housing.

In another embodiment of the invention, the notches on the housing are adapted to receive the said first locking mechanism and the second locking mechanism are provided respectively on the same side of the housing.

In a further embodiment of the invention, the knob and the mechanisms are integral enabling movement of the blade carrier and locking simultaneously.

BRIEF DESCRIPTION OF THE ACCOMPANYING DRAWINGS

FIGS. 5A and 5B are schematic representations of the rear end stopper provided on the housing showing taper wedge for disposable locking.

DETAILED DESCRIPTION OF THE INVENTION

In the operating room, surgical scalpels are often transferred back and forth between the operating surgeon and the other personnel assisting in the operation. The transfer of instruments during surgery is often dictated by considerations of speed. As such, the use of scalpels during surgery often result in cuts and nicks due to the rapid transfer from one person to another. The spread of communicable diseases such as Hepatitis and AIDS and other blood carried diseases has rendered the operation theater fraught with risk for the operating personnel. It is therefore important to devise instruments, which avoid or at least minimize substantially the risk of operating room personnel being infected with communicable diseases due to accidental injuries suffered during the course of operation.

Similarly, after the completion of the surgical procedures, it has now become mandatory whether by way of statutory regulations or in house policies of most hospitals to dispose of instruments such as scalpels which are invasive and have come into direct contact with the patient. Disposal of such instruments such as scalpels poses a problem due to the sharp cutting edge of the blade. Disposal therefore inevitably requires tremendous safety precautions and it is not unknown for accidental cuts and nicks to occur during disposal of such instruments to the persons handling such equipment.

The present invention is a disposable safety scalpel with a retractable blade and a novel locking mechanism. The invention will be described in detail below with reference to the accompanying drawings.

Figure 1:
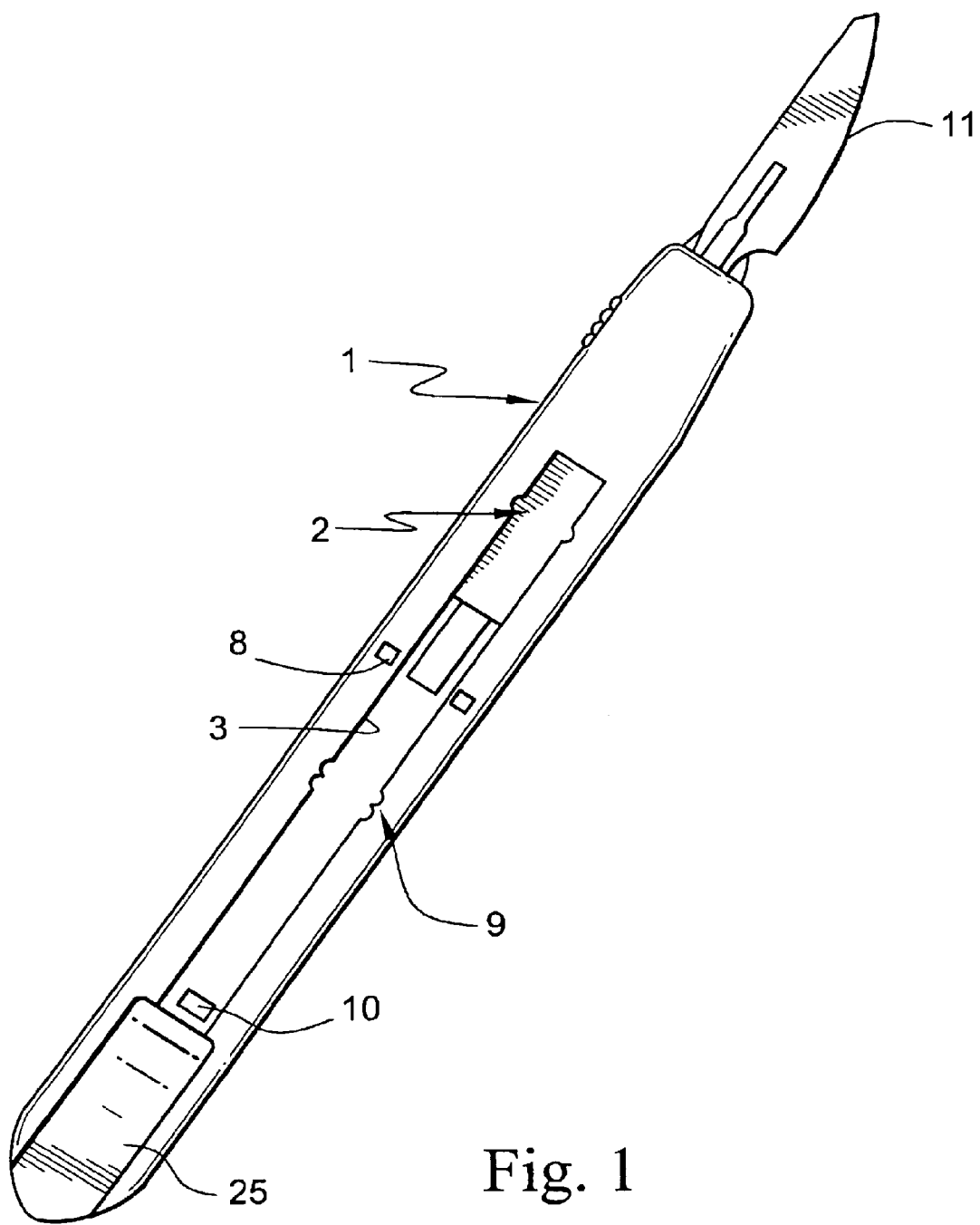
FIG. 1 is an isometric view of the disposable safety scalpel of the invention with the blade shown in a cutting position.

Referring now to FIG. 1, an isometric view of the disposable safety scalpel according to the invention is shown with the blade being displayed in a cutting or operating position.

The housing (1) is provided with a groove (3) which holds the blade carrier (2). The blade carrier (2) is provided with a knob (not shown in detail in FIG. 1) which is slideable in the groove or elongated opening (3) from a first in use position (shown) to a second pass position (not shown) and after use to a final disposal position (not shown) where the blade is permanently locked. The safety scalpel is also provided with a first locking means (8) to ensure locking of the blade carrier in the housing in the in use position, a second locking means or positioning lug receptacle (9) to ensure locking in the pass position, and a third locking means (10) is provided to ensure permanent locking of the blade carrier (2) with the blade (11) in a retracted position (not shown) when the scalpel is ready for disposal. As a result of the permanent disposal locking position, the safety of handlers during disposal is ensured. Similarly, the easy locking transfer between the pass position and the in use position ensures that transfer of the scalpel during operation does not result in any accidental nick or cut to the user or handler.

Figure 2:
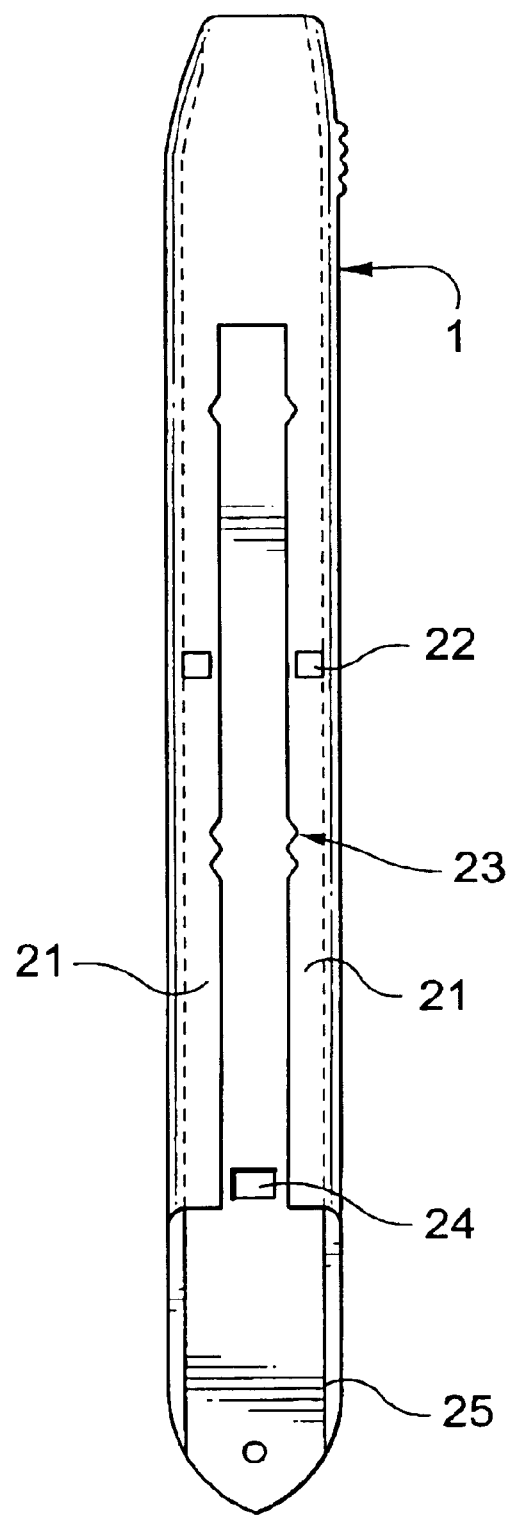
FIG. 2 is a schematic representation of the housing with the groove shown to enable the carrier to slide. The housing has a bottom, two side walls and two flanges at the top showing the in use locking position and a groove between the flanges for actuating the knob for the lateral movement of the carrier.

FIG. 2 is a schematic representation of the housing with the different locking positions indicated thereon. The housing (1) is provided with a first pair of slots (22) remote from the elongated opening 3 (as shown in FIG. 1) to enable locking of the blade carrier (not shown in FIG. 2) in a first in use position. Since the slots or arm lug receptacles (22) are engaged in a relatively rigid manner by the corresponding arm lug portions provided on the blade carrier, the actual positive force required to be applied by the user will not cause unlocking of the blade carrier from the first in use position to the second pass position. This ensures that the blade carrier remains in a rigid position in actual use and the potential of the accidental retraction during surgery is avoided. The release of the in use locks by the natural forces of retraction necessary to bring the carrier to the pass position. At each stage of the surgical procedure requiring the use of the scalpel, the blade carrier can be retracted to a pass position (23) where a releasable locking means is provided. This ensures the safety of those assisting personnel who handle the scalpel after the completion of the specific surgical maneuver. After the completion of the entire surgical procedure, the blade carrier can be retracted to a third and final locking position comprising a slot or notch (24) provided near the end stopper (25). This permanent locking ensures that the potential for accidental nicks and cuts during post operative disposal of used surgical instruments is avoided.

Figure 3:
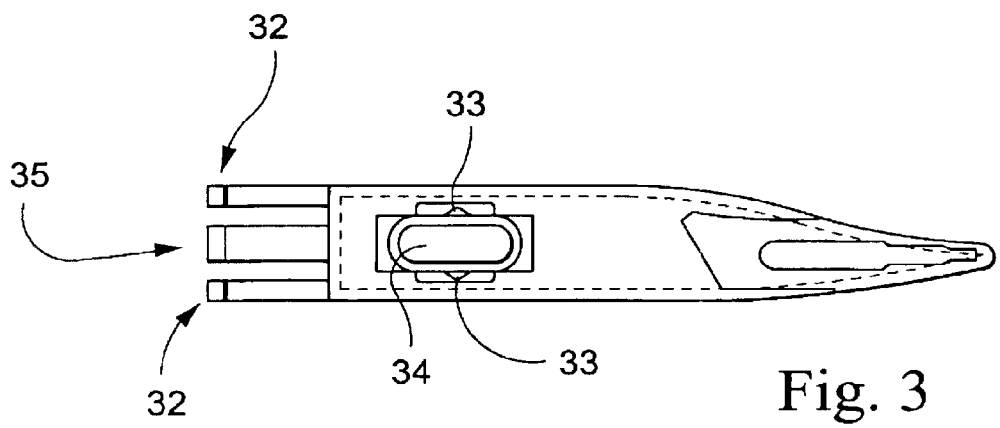
FIG. 3 is a schematic representation of the blade carrier without the blade showing the different locking means provided thereon.

FIG. 3 is a schematic representation of the blade carrier without the blade showing the different locking means provided thereon. The first locking means (32) cooperates with the corresponding pair of slots (22) provided on the housing (see FIG. 2) to ensure a rigid locking during in use position for the blade carrier (2). This ensures that accidental retraction of the blade (11) during actual surgical maneuver does not occur. However, the blade can be retracted from the first in use position by direct application of force on an actuator comprising a knob (34) to release the first locking means from the corresponding slots provided on the housing. The blade then retracts into the pass position and stays locked therein due to the second locking means or positioning lugs (33) provided on the blade carrier. Since the second locking means is releasable, the scalpel can be reused during the same surgical procedure by simply pushing the knob to move in the groove provided on the housing (not shown) to push the blade into a first in use position. After final completion of the surgical procedure, the blade carrier is pushed back to a final permanent locking position where a third locking means or leg element (35) provided on the blade carrier engage the notch or lug receptacle (24) on the housing (1) to ensure permanent locking. In this final stop position, the blade carrier cannot be released accidentally, thereby ensuring complete safety of the operator.

Figure 4A:
FIGS. 4A and 4B are schematic representations of the knob provided on the blade carrier with the respective locking means for pass and in use stages shown thereon.
Figure 4B:
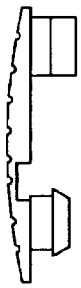
Figure 6:
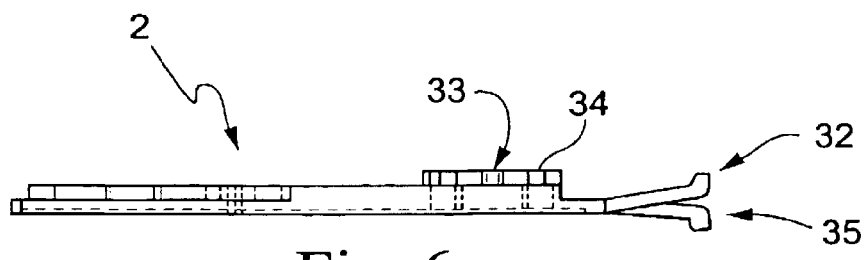
FIG. 6 is a schematic representation of the blade carrier with the knob and the locking means being integral inter se.

FIGS. 4A and 4B are schematic representations of the knob provided on the blade carrier with the respective locking means for safe, in use and post use stages shown thereon. Referring to FIGS. 2 and 6, the knob (34) is used for exposing and retracting the blade as required. The in use lock component(s) (32) are pressed into the slots (22) provided in the two flanges (21) of the housing. During in use position, the lock components (32) engage two slots (22) provided on the housing and the elasticity of the plastic carrier spring ensures firm locking during this position. The firm locking and the close tolerance between the hollow handle and the slideable carrier (2) provide stability to the blade during the surgical procedure. After use, the blade can be retracted. The movement of the knob (34) in the groove (3) provided on the housing first releases the in use lock by downward pressure. The knob is provided with two pads for the specific application of pressure in a downward direction on the first locking means to ensure their release. Further retraction of the blade after release from the in use position brings the blade carrier to a second pass position where the locking means is a releasable locking means (23,33). If the scalpel is required again during the surgical procedure, the blade carrier can simply be extended to the in use position where the first locking means operates as described above. If the scalpel is not required any longer, the blade carrier can simply be retracted by actuation using the knob to a final stop position where the third locking means, locking leg (35), engages slot (24) to ensure permanent locking of the blade carrier. As can be seen from FIG. 2, slot (24) is defined on the opposite side of housing (1) from slots (22). At this stage, the scalpel is ready for disposal with no risk of any accidental injury. In one embodiment the knob and the locking means are integral (see FIG. 6).

Figure 5A:
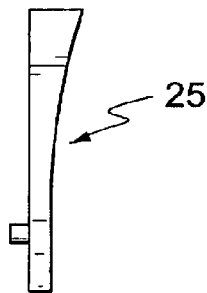
Figure 5A:
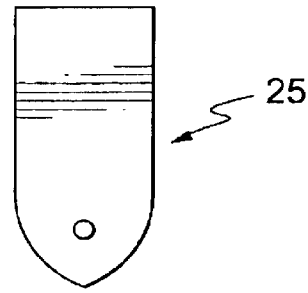

FIG. 5 is a schematic representation of the rear end stopper provided on the housing to ensure disposable locking. The operation of the rear end stopper is to ensure a permanent locking of the blade carrier after completion of the surgical procedure where the blade is ready for disposal.

FIG. 6 is a schematic representation of the blade carrier with the knob and the locking means being integral. The blade carrier (2) is provided with the knob (34) located centrally on the flat portion thereon. The knob functions to push the blade carrier between the various operative and non-operative (pass and disposal positions) on the application of an actuating force by the user. The locking at the various positions (operative, pass, and disposal) is provided with respective locking means (32,33, and 35 respectively).

The embodiments described above are illustrative and various modifications are possible within the scope and spirit of the invention. The figures describe specific preferred embodiments and should not be construed as limiting the scope of the invention in any manner.

We claim:

1. A disposable safety scalpel comprising a housing, a blade carrier with a scalpel blade fixedly provided at an end thereof, the blade carrier being slidably provided in the housing, the housing being provided with a proximal open end to enable sliding in and out of the blade carrier to expose a cutting edge of the scalpel blade and a distal closed end, a plurality of corresponding locking elements being provided on the blade carrier and on the housing to enable locking of the blade carrier in three positions of pre-use, actual use and post use disposal, said blade carrier also being provided with an actuator to enable displacement of the blade carrier along the housing, the housing being provided with an elongated opening through which the actuator extends, wherein the plurality of corresponding locking elements comprise at least one arm element provided on the blade carrier and extending in a longitudinal direction thereof, said arm element having a lug portion for selectively engaging a corresponding arm lug receptacle, said arm lug receptacle being remote from said elongated opening.

2. A disposable safety scalpel as claimed in claim 1 wherein said actuator comprises a knob configured to enable positive movement of the blade carrier from the pre-use position to the actual use position and finally to the post-use disposal position.

3. A disposable safety scalpel as claimed in claim 1 wherein said locking elements comprise, for defining the pre-use position, at least one positioning lug provided on the blade carrier and cooperating with a corresponding positioning lug receptacle provided on said housing to ensure releasable locking.

4. A disposable safety scalpel as claimed in claim 3, wherein the at least one positioning lug receptacle and the arm lug receptacle are provided respectively on the same side of the housing.

5. A disposable safety scalpel as claimed in claim 1 wherein the locking elements comprise at least a pair of said arm elements extending in the longitudinal direction from the end of the blade carrier opposite the blade end and provided with said lug portions for cooperating with a corresponding pair of said arm lug receptacles provided on said housing, said lug receptacles being adapted to receive the lug portions on said arm elements and retain them therein securely until actual release by the user.

6. A disposable safety scalpel as claimed in claim 5, wherein the arm lug receptacles on the housing adapted to receive said lug portions of said arm elements are provided respectively on opposite sides of the elongated opening in said housing.

7. A disposable safety scalpel as claimed in claim 5, wherein the actuator is provided with an actuating means to enable release of the blade carrier from the actual use position to the post use disposal position by actual retraction force.

8. A disposable safety scalpel as claimed in claim 7, wherein the actuating means is provided on said blade carrier and comprises a knob.

9. A disposable safety scalpel as claimed in claim 8, wherein the knob and the arm elements of the blade carrier are integral enabling movement of the blade carrier and locking simultaneously.

10. A disposable safety scalpel as claimed in claim 1, wherein the housing has a bottom and two side walls with a groove running from one end to the other to enable sliding movement of the blade carrier.

11. A disposable safety scalpel as claimed in claim 1, wherein said corresponding locking elements further comprise at least one leg element resiliently provided on said blade carrier for engaging a corresponding receptacle provided on said housing, engagement of said resilient leg element with said corresponding leg receptacle defining said post use disposal position of said blade carrier.

12. A disposable safety scalpel as claimed in claim 11, wherein said arm lug receptacle and said leg receptacle are respectively provided on opposite sides of the housing.

13. A disposable safety scalpel comprising a housing, a blade carrier with a scalpel blade fixedly provided at an end thereof, the blade carrier being slidably provided in the housing, the housing being provided with a proximal open end to enable sliding in and out of the blade carrier to expose a cutting edge of the scalpel blade and a distal closed end, a plurality of corresponding locking elements being provided on the blade carrier and on the housing to enable locking of the blade carrier in three positions of pre-use, actual use and post use disposal, wherein the locking elements comprise at least a pair of matched arms extending in the longitudinal direction from the end of the blade carrier opposite the blade end and provided with lug portions cooperating with a corresponding pair of lug slots provided on said housing to define the actual use position, said lug slots being adapted to receive the lug portions on said arms and retain them therein securely until actual release by user a user.

14. A disposable safety scalpel as claimed in claim 13, wherein said locking elements comprise, for defining the pre-use position, at least one positioning lug provided on the blade carrier and cooperating with a corresponding positioning lug receptacle provided on said housing to ensure releasable locking.

15. A disposable safety scalpel as claimed in claim 14, wherein the at least one positioning lug receptacle and the lug slots are provided respectively on the same side of the housing.

16. A disposable safety scalpel as claimed in claim 13, wherein the blade carrier is provided with an actuator to enable release of the blade carrier from the actual use position and movement to the post use disposal position.

17. A disposable safety scalpel as claimed in claim 13, wherein the pair of slots on the housing adapted to receive the lug portions of said arms are laterally spaced from one another on a common side of the housing.

18. A disposable safety scalpel as claimed in claim 13, wherein said corresponding locking elements further comprise at least one leg element resiliently provided on said blade carrier for engaging a corresponding leg receptacle provided on said housing, engagement of said resilient leg element with said corresponding leg receptacle defining said post use disposal position of said blade carrier, wherein said lug slots and said leg receptacle are respectively provided on opposite sides of the housing.

* * * * *